United States Patent
Okamoto

(10) Patent No.: US 9,412,500 B2
(45) Date of Patent: Aug. 9, 2016

(54) ELECTROSTATIC COATING CABLE MAINTENANCE DEVICE

(71) Applicant: Ransburg Industrial Finishing K.K., Kanagawa (JP)

(72) Inventor: Kenji Okamoto, Kanagawa (JP)

(73) Assignee: Ransburg Industrial Finishing K.K., Kanagawa (JP)

(*) Notice: Subject to any disclaimer, the term of this patent is extended or adjusted under 35 U.S.C. 154(b) by 244 days.

(21) Appl. No.: 14/379,499

(22) PCT Filed: Feb. 18, 2013

(86) PCT No.: PCT/JP2013/053831
§ 371 (c)(1),
(2) Date: Aug. 19, 2014

(87) PCT Pub. No.: WO2013/125478
PCT Pub. Date: Aug. 29, 2013

(65) Prior Publication Data
US 2015/0027370 A1    Jan. 29, 2015

(30) Foreign Application Priority Data

Feb. 20, 2012 (JP) ................................. 2012-034570
Sep. 24, 2012 (JP) ................................. 2012-209496

(51) Int. Cl.
| | |
|---|---|
| *G01R 31/00* | (2006.01) |
| *H01B 13/00* | (2006.01) |
| *B05B 5/053* | (2006.01) |
| *G01N 19/08* | (2006.01) |
| *H01B 9/00* | (2006.01) |
| *G01R 31/02* | (2006.01) |

(52) U.S. Cl.
CPC ............ *H01B 13/0033* (2013.01); *B05B 5/053* (2013.01); *G01N 19/08* (2013.01); *G01R 31/021* (2013.01); *G01R 31/026* (2013.01); *H01B 9/00* (2013.01); *H01B 13/0036* (2013.01)

(58) Field of Classification Search
CPC .... G01N 19/08; G01R 31/021; G01R 31/026; H01B 13/0033; H01B 13/0036; H01B 9/00
USPC ......................................... 324/539, 541, 457
See application file for complete search history.

(56) References Cited

U.S. PATENT DOCUMENTS

| | | | |
|---|---|---|---|
| 3,284,704 A | 11/1966 | Lamont | |
| 4,627,076 A * | 12/1986 | Staal | ...................... H01B 11/00 375/257 |

(Continued)

FOREIGN PATENT DOCUMENTS

| | | |
|---|---|---|
| JP | H01-213039 A | 8/1989 |
| JP | H07-027811 A | 1/1995 |

(Continued)

OTHER PUBLICATIONS

Supplementary European Search Report received in corresponding European Patent Application No. 13751202.6 dated Nov. 9, 2015 (6 pages).

*Primary Examiner* — Vincent Q. Nguyen
(74) *Attorney, Agent, or Firm* — Kilyk & Bowersox, P.L.L.C.

(57) ABSTRACT

A time period required for replacement work of a divided cable is shortened. An electrostatic coating cable (6) includes a power supply line (12) that supplies power to a high voltage generator (2), a signal line (14) that controls the high voltage generator (2), and a ground line (16). The power supply line (12) and the ground line (16) are connected by a first inspection line (18), the signal line (14) and the ground wire (16) are connected by a second inspection line (20), a first diode (22) is interposed in the first inspection line (18), and a second diode (24) is interposed in the second inspection line (20). The first and the second diodes (22) and (24) inhibit a current from flowing through the first and the second inspection lines (18) and (20) during an operation of the electrostatic coater (1). The first and the second inspection lines (18) and (20) and the first and the second diodes (22) and (24) are contained in a cable connecting section (8) that connects divided cables (10) adjacent to each other. During stoppage of the electrostatic coater (1), a voltage for inspection is applied to the ground line (16).

6 Claims, 9 Drawing Sheets

(56) References Cited

U.S. PATENT DOCUMENTS

| | | | |
|---|---|---|---|
| 5,793,588 A * | 8/1998 | Jeong | H01L 27/0266 361/111 |
| 2009/0108109 A1 | 4/2009 | Mori et al. | |
| 2012/0187957 A1 | 7/2012 | Yamasaki et al. | |

FOREIGN PATENT DOCUMENTS

| | | |
|---|---|---|
| JP | H10-109054 A | 4/1998 |
| JP | 2002-186884 A | 7/2002 |
| JP | 2007-029920 A | 2/2007 |

* cited by examiner

ELECTROSTATIC COATING CABLE MAINTENANCE DEVICE

The present application is a National Stage Application of PCT/JP2013/053831, filed Feb. 18, 2013, which claims priority from Japanese Patent Application No. 2012-034570, filed Feb. 20, 2012 and Japanese Patent Application No. 2012-209496 filed Sep. 24, 2012.

BACKGROUND OF THE INVENTION

The present invention relates to electrostatic coating, and more particularly to an electrostatic coating cable maintenance device that detects a part having a conduction failure including breakage of a cable that connects a high voltage generator included in an electrostatic coater with a control panel installed at an exterior of a coating booth.

Electrostatic coating has the characteristic of having excellent coating efficiency since an atomized coating material is electrically charged and the electrically charged coating material is electrically attached to an object to be coated as is well known, and is widely used in coating of automobile bodies. Since a high voltage is indispensable for an electrostatic coating system, various maintenance steps are performed against leakage of a high voltage and for proper voltage application.

In order to cope with the problem of high voltage leakage caused by adherence of a coating material to the outer surface of an electrostatic coater, Japanese Patent Laid-Open No. 10-109054 proposes that a reference electrode is prepared at a position away from a high-voltage application electrode of the electrostatic coater, and when it is predicted that electrically charged coating material particle is in a state easily adhering to an electrostatic coater main body based on the value of a current flowing in the reference electrode, a coating state is controlled by controlling an ejection amount of the coating material, stopping application of a high voltage, stopping carrying-in of an object to be coated and the like.

In order to alleviate the problem caused by adherence of a coating material to the outer surface of an electrostatic coater, Japanese Patent Laid-Open No. 2002-186884 proposes detecting the amplitude of a current flowing in a high voltage application path which includes a high voltage generator contained in the electrostatic coater, integrating the amplitude values of the current for a fixed time period when the amplitude of the current exceeds a predetermined value, and issuing an alarm when the integrated value exceeds a predetermined value.

In order to cope with the problem of high voltage leakage caused by adherence of a coating material to the outer surface of an electrostatic coater that is incorporated in a coating robot, Japanese Patent Laid-Open No. 2007-29920 proposes connecting a lead wire to a cable connecting section that is provided at an end plate of the electrostatic coater, and detecting high voltage leakage through the lead wire. Further, Japanese Patent Laid-Open No. 2007-29920 discloses an entire outline of a maintenance device that is incorporated in a control panel that controls the electrostatic coater, for monitoring the electrostatic coater, and by the maintenance device, propriety of feedback control of a high voltage to be applied to the electrostatic coater, various kinds of high voltage leakage and the like are monitored.

SUMMARY OF THE INVENTION

In coating systems for automobile bodies, coating robots installed in coating booths are generally adopted. A coating robot includes, at a distal end of an arm thereof, an electrostatic coater containing a high voltage generator therein. The electrostatic coater is connected to a control panel installed outside the coating booth through a cable, and control of the coating robot including the electrostatic coater is executed by the control panel. The electrostatic coating cable that electrically connects the control panel and the electrostatic coater includes power supply line that supplies power to the high voltage generator contained in the electrostatic coater, a plurality of signal lines and a ground line, and control of the electrostatic coater is executed through the cable.

Since a control panel and an electrostatic coater are sometimes located by being spaced from each other, and the electrostatic coating cable that connects the control panel and the electrostatic coater is generally configured by connecting a plurality of divided cables in series. For example, when an electrostatic coating cable is configured by three divided cables, a first divided cable is disposed between a coating robot and a control panel, two of a second and a third divided cables are disposed inside the coating robot, and the first to the third divided cables are connected in such a manner that the divided cables adjacent to each other is connected by each connector.

When a problem occurs to the power supply line, the signal lines or the ground line contained in the electrostatic coating cable, namely, when a line contained in the electrostatic coating cable is almost broken, the corresponding line has a large resistance, and the action of the electrostatic coater becomes unstable. Therefore, it can be known that a problem occurs to the electrostatic coating cable by the aforementioned maintenance device. Subsequently, replacement work of the electrostatic coating cable is carried out to cope with the problem. As a matter of course, replacement of the electrostatic coating cable is performed in a state in which a coating line is stopped.

The replacement work of the electrostatic coating cable is started from identifying to which divided cable the problem occurs. When the corresponding divided cable can be identified, replacement of the divided cable is performed. The series of replacement work is performed in the state in which the coating line is stopped, and therefore, the replacement work is urgent work in which every second counts.

An object of the present invention is to provide an electrostatic coating cable maintenance device that can reduce a time required for replacement work of a divided cable.

According to a first aspect of the present invention, the above described technical problem is achieved by providing an electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line and a ground line, and the power supply line or the signal line that configures the cable being brought into a state immediately before breakage, wherein in a plurality of wires that configure the power supply line, the signal line and the ground line, two wires having a potential difference during an operation of the electrostatic coater are set as a pair, and the two lines that configure each pair are connected by an inspection line, a diode is interposed in the inspection line, and the diode inhibits a current from flowing between the two lines during the operation of the electrostatic coater, the electrostatic coating cable maintenance device comprises faulty divided cable identifying means that, during stoppage of the operation of the electrostatic coater, applies a voltage to the inspection line connecting the two lines of each pair to pass a current through the inspection line, detects feedback signals that return from the respective two lines, and identifies the divided cable which is brought into a state immediately before breakage based on abnormality of the feedback signals, and the inspection line and the diode are disposed in a cable connecting section that connects the divided cables adjacent to each other.

According to a second aspect of the present invention, the above described technical problem is achieved by providing an electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line and a ground wire, and the power supply line or the signal line that configures the cable being brought into a state immediately before breakage, the electrostatic coating cable maintenance device having:

a first inspection line that connects the ground line and the power supply line;

a second inspection line that connects the ground line and the signal line;

a first diode that is interposed in the first inspection line, and cuts off a flow of a current between the power supply line and the ground line during an operation of the electrostatic coater;

a second diode that is interposed in the second inspection line, and cuts off a flow of a current between the signal line and the ground line during the operation of the electrostatic coater;

a ground switch that is provided in the ground line, and can switch to a first mode that grounds the ground wire, and a second mode that applies a voltage to the ground line; and faulty divided cable identifying means that, during stoppage of the operation of the electrostatic coater, detects feedback signals that return from the power supply line and the signal line when a voltage is applied to the ground line in a state in which the switch is switched to the second mode from the first mode, and identifies the divided cable which is brought into a state immediately before breakage based on abnormality of the feedback signal, wherein the first and the second inspection lines and the first and the second diodes are disposed in a cable connecting section that connects the divided cables adjacent to each other.

FIG. 1 is a view for explaining a basic concept of the second aspect of the present invention. Reference numeral 1 designates an electrostatic coater. The electrostatic coater 1 is mounted to a coating robot installed in a coating booth, and performs coating of an automobile body. A high voltage generator 2 contained in the electrostatic coater 1 is connected to a control panel 4 via an electrostatic coating cable 6. As shown in FIG. 2, the electrostatic coating cable 6 is configured by a first to a third divided cables 10 connected by cable connecting sections 8. The number of divided cables 10 may be two, four or the like. In order to identify the divided cable 10, the first divided cable is assigned with NO. 1, the second divided cable is assigned with NO. 2, and the third divided cable is assigned with NO. 3.

Referring to FIG. 2, the electrostatic coating cable 6 includes a power supply line 12 that supplies power to the high voltage generator 2, a signal line 14 that controls the high voltage generator 2, and a ground line 16. The power supply line 12 and the ground line 16 are connected by a first inspection line 18. The signal line 14 and the ground line 16 are connected by a second inspection line 20. In the first inspection line 18, a first diode 22 is interposed, and in the second inspection line 20, a second diode 24 is interposed. The first and the second diodes 22 and 24 respectively inhibit a current from flowing through the first and the second inspection lines 18 and 20 during an operation of the electrostatic coater 1. Thereby, the electrostatic coater 1 can be operated normally.

The first inspection line 18 and the first diode 22 are contained in a first cable connecting section 8 (NO. 1) that connects the first and the second divided cables 10 (NO. 1 and NO. 2). The second inspection line 20 and the second diode 24 are contained in a second cable connecting section 8 (NO. 2) that connects the second and the third divided cables 10 (NO. 2 and NO. 3).

In the control panel 4, faulty divided cable identifying means 30 is incorporated. More specifically, the faulty divided cable identifying means 30 is configured by a high voltage controller IC. The faulty divided cable identifying means 30 applies a voltage for inspection to the ground line 16 when power is not supplied to the electrostatic coater 1, for example, before start of the operation or after end of the operation of the coating booth, or during stoppage of the operation of the electrostatic coater 1 or the like. A ground switch 32 is interposed in the ground line 16 to release a grounded state of the ground line 16. The ground switch 32 is switched to an off state prior to application of an inspection voltage to the ground line 16. The faulty divided cable identifying means 30 determines to which divided cable 10 (NO. 1, NO. 2, or NO. 3) a problem occurs in accordance with feedback signals, namely, voltage or current values that return from the power supply line 12 and the signal line 14 by applying the inspection voltage to the ground line 16. The inspection of the electrostatic coating cable 6 is automatically executed based on a manual operation by a user or at a predetermined time point during stoppage of the electrostatic coater 1.

FIG. 3 illustrates a case in which a problem occurs to the power supply line 12 of the third divided cable 10 (No. 3). Referring to FIG. 3, an inspection voltage $V_0$ that is applied to the ground line 16 is fed back to the faulty divided cable identifying means 30 through the first and the second inspection lines 18 and 20 before reaching the electrostatic coater 1. Internal resistances of the first and the second diodes 22 and 24 which are interposed in the first and the second inspection lines 18 and 20 are illustrated by $R_0$. A combined internal resistance $R_a$ of the two first diodes 22 in total which are contained in the first and the second cable connecting sections 8 relating to the power supply line 12 can be obtained by the following expression under the condition that the relation to other related elements is ignored.

$$R_a = 1/\{(1/R_0)+(1/R_0)\} = 1 0/(2/R_0) = R_0/2$$

Accordingly, when the inspection voltage to be applied to the ground line 16 is $V_0$, a feedback voltage $V_a$ that returns to the faulty divided cable identifying means 30 through the power supply line 12 can be expressed by the following equation if the relation with the other related elements is ignored.

$$V_a = Ia \cdot R_0/2$$

The above described "Ia" represents a current value.

Substantially the same thing as what is mentioned above applies to a case in which a problem occurs to the signal line 14 of the third divided cable 10 (No. 3).

FIG. 4 illustrates a case in which a problem occurs to the power supply line 12 of the second divided cable 10 (No. 2). Referring to FIG. 4, the voltage that is applied to the ground line 16 returns to the faulty divided cable identifying means 30 through the first inspection wire 18 of the first cable connecting section 8 (No. 1) before reaching the second cable connecting section 8 (No. 2). The internal resistance of the first diode 22 of the first inspection line 18 relating to the power supply line 12 of the first cable connecting section 8 (No. 1) is $R_0$ that is mentioned above. The feedback voltage $V_a$ that returns to the faulty divided cable identifying means 30 when a problem occurs to the power supply line 12 of the second divided cable 10 (No. 2) can be expressed by the following equation if the relation with the other related elements is ignored.

$$V_a = Ib \cdot R_0$$

The above described "Ib" represents a current value.

Substantially the same thing as what is mentioned above applies to a case in which a problem occurs to the signal line 14 of the second divided cable 10 (No. 2).

Note that when a problem occurs to the first divided cable 10 (No. 1) which is the closest to the faulty divided cable identifying means 30, the inspection voltage that is applied to the ground line 16 is not fed back to the faulty divided cable identifying means 30, when explanation is made with an example in which a part of line of the first divided cable 10 is completely broken, for example, to simplify the explanation.

The above described explanation is very simplified explanation by using the case in which any one of the first to the third divided cables 10 (No. 1 to No. 3) is broken as an example, and omitting the influence of transformers and the like that are the other related elements. When the power supply line 12 or the signal line 14 is almost broken, a feedback voltage cannot be expressed by a mathematical expression uniformly because the resistance of the part which is almost broken is included. In any case, however, when any one of the first to the third divided cables 10 (No. 1 to No. 3) is almost broken, a difference (abnormality) from a signal at a normal time occurs to a signal (the feedback voltage $V_a$ in the above described example) that is fed back to the faulty divided cable identifying means 30, in a case in which breakage occurs to the first divided cable 10 (No. 1), a case in which breakage occurs to the second divided cable 10 (No. 2), and a case in which breakage occurs to the third divided cable 10 (No. 3). By using the difference (abnormality) in the voltage value of the feedback voltage $V_a$, the divided cable which is almost broken can be identified. As the feedback signal, a current value may be adopted.

In order to clarify a difference in the signal (the feedback voltage $V_a$ in the above described example) which is fed back to the faulty divided cable identifying means 30 at the time of occurrence of a problem to any one of the first to the third divided cables 10, an additional resistance may be provided at the first inspection line 18, an additional resistance may be provided at the second inspection line 20, or resistances may be provided at both of the first and the second inspection lines 18 and 20. When the resistances are provided at both of the first and the second inspection lines 18 and 20, the resistances to be adopted may have the same resistance value or may have different resistance values.

Further, the aforementioned additional resistance may be provided at only the first inspection line 18 and/or the second inspection line 20 of the first cable connecting section 8 (No. 1), or the aforementioned additional resistance may be provided at only the first inspection line 18 and/or the second inspection line 20 of the second cable connecting section 8 (No. 2), or the aforementioned additional resistances may be provided at the first inspection lines 18 and/or the second inspection lines 20 included in both of the first cable connecting section 8 (No. 1) and the second cable connecting section 8 (No. 2).

In regard with setting of the resistance value of the additional resistance, the respective additional resistance values can be set as follows, for example. The resistance values of the additional resistances described above can be set so that the feedback voltage $V_a$, for example, in the case in which a problem occurs to the first divided cable 10 (No. 1) is at a potential higher than the feedback voltage at a time of all the divided cables 10 (No. 1 to No. 3) being normal, the feedback voltage $V_a$ in the case in which a problem occurs to the second and the third divided cables 10 (No. 2 and No. 3) is at a potential lower than the feedback voltage at a time of all the divided cables 10 (No. 1 to No. 3) being normal, and further, a clear difference appears in the feedback voltages $V_a$ at the time in which a problem occurs to the second divided cable 10 (No. 2) and a problem occurs to the third divided cable 10 (No. 3).

Note that while in the illustrated example, the ground line 16 is illustrated as a common ground line, a ground line to which the power supply line 12 is connected via the first inspection line 18 and a ground line to which the signal line 14 is connected via the second inspection line 20 may be separate.

According to a third aspect of the present invention, the above described technical problem is achieved by providing an electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line in which a signal at a potential with polarity opposite to polarity of the power supply line flows during an operation of the electrostatic coater, and a ground line, and the power supply line or the signal line that configures the cable being brought into a state immediately before breakage, the electrostatic coating cable maintenance device having:

a third inspection wire that connects the signal line and the power supply line during the operation of the electrostatic coater;

a fourth inspection line that connects the signal line and the ground line during the operation of the electrostatic coater;

a third diode that is interposed in the third inspection wire, and cuts off a flow of a current between the power supply line and the signal line during an operation of the electrostatic coater;

a fourth diode that is interposed in the fourth inspection line, and cuts off a flow of a current between the signal line and the ground line during the operation of the electrostatic coater;

a ground switch that is provided in the ground line, and can switch to a first mode that grounds the ground line, and a second mode that applies a voltage to the ground line; and faulty divided cable identifying means that, during stoppage of the operation of the electrostatic coater, detects feedback signals that return from the power supply line and the ground line when a voltage is applied to the signal line in a state in which the switch is switched to the second mode from the first mode, and identifies a divided cable which is brought into a state immediately before breakage based on abnormality of the feedback signals, wherein the third and the fourth inspection lines and the third and the fourth diodes are disposed in a cable connecting section that connects the divided cables adjacent to each other.

According to the invention according to the third aspect, the divided cable in which the ground line is almost broken can be detected. Further, the electrostatic coater can be normally operated by the third and the fourth diodes. A person skilled in the art could grasp an operation and effect of the invention according to the third aspect by reading explanation of a second embodiment that will be described later.

EXPLANATION OF REFERENCE NUMERALS

Figure 1:
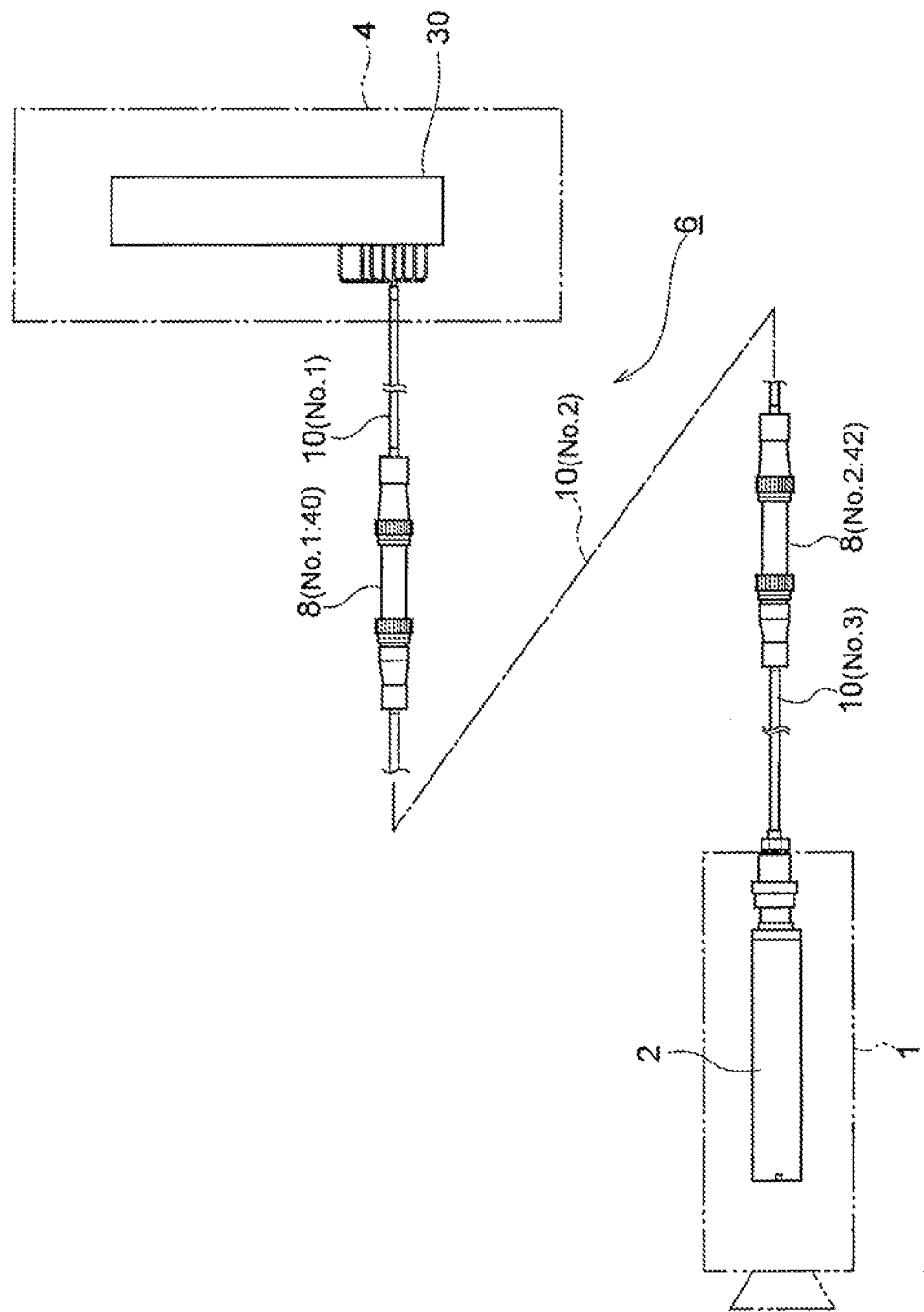
FIG. 1 is a diagram for explaining an entire outline of an electrostatic coating cable maintenance device according to the present invention.

1 Electrostatic coater
2 High voltage generator
4 Control panel
6 Electrostatic coating cable
8 Cable connecting section
8(No. 1) First cable connecting section
8(No. 2) Second cable connecting section
10 Divided cable
10(No. 1) First divided cable
10(No. 2) Second divided cable
10(No. 3) Third divided cable
12 Power supply line
14 Signal line
16 Ground line
18 First inspection line
20 Second inspection line
22 First diode
24 Second diode
30 Faulty divided cable identifying means (high voltage controller IC)
32 Ground switch
Rad Additional resistor

BEST MODE FOR CARRYING OUT THE INVENTION

Hereinafter, preferable embodiments of the present invention will be described based on the accompanying drawings.

Referring to FIG. 1 again, in an electrostatic coating cable maintenance device of the embodiment, an electrostatic coating cable 6 is configured by connecting three divided cables 10 (No. 1 to No. 3) in series with use of relay boxes 40 and 42 in a first and a second connecting sections 8 (No. 1 and No. 2). More specifically, the first connecting section 8 (No. 1) is configured by the first relay box 40 including an internal structure illustrated in FIG. 6, and the second connecting section 8 (No. 2) is configured by the second relay box 42 including an internal structure illustrated in FIG. 7.

Figure 5:
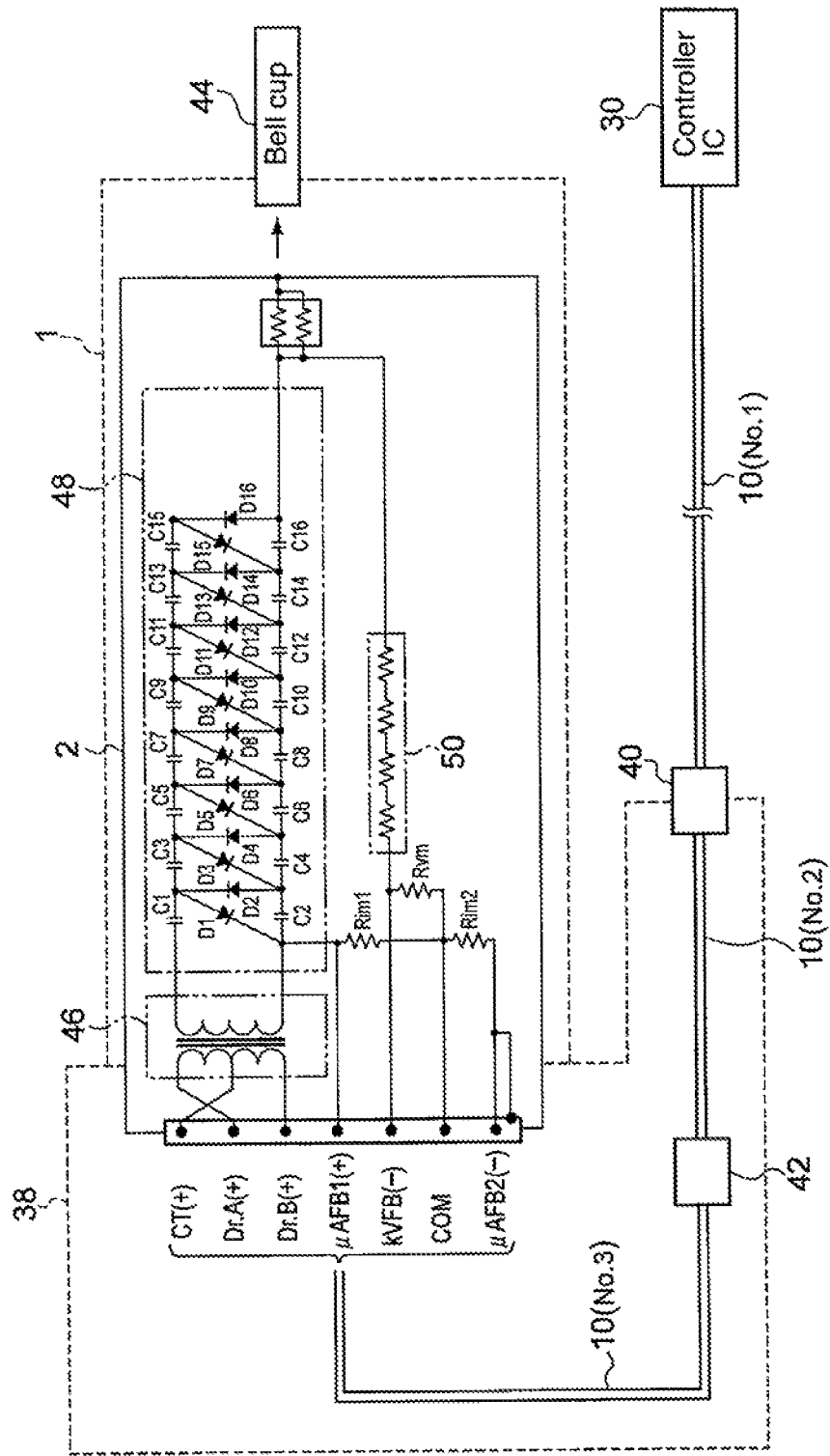
FIG. 5 is a diagram for explaining an entire outline of the electrostatic coating cable maintenance device according to the present invention.

FIG. 5 shows a configuration of a high voltage generator 2 contained in an electrostatic coater 1 to which the electrostatic coating cable maintenance device of the embodiment is applied. Reference numeral 38 shown in FIG. 5 designates a coating robot. Referring to FIG. 5, the electrostatic coating cable maintenance device of the embodiment is applied to a rotary atomization type electrostatic coater, and a high voltage generated by the high voltage generator 2 is applied to a bell cup 44 that is a rotary atomizing head.

The high voltage generator 2 includes a transformer 46 and a Cockcroft-Walton circuit 48. A high voltage (for example, minus 90,000 volts) of negative polarity (minus) that is boosted by the Cockcroft-Walton circuit 48 is supplied to the bell cup 44. In the drawing, reference numeral 50 designates a bleeder resistance.

To the high voltage generator 2, three lines 12 are connected as a power supply line. To the high voltage generator 2, three signal lines 14 for controlling the high voltage generator 2 and a common ground line 16 are connected similarly to the conventional electrostatic coater. These lines are connected to a control panel 4 through the first to the third divided cables 10 (No. 1 to No. 3). When a problem occurs to the electrostatic coating cable 6, which divided cable of the first to the third divided cables 10 (No. 1 to No. 3) the problem occurs to is identified by faulty divided cable specifying means (high voltage controller IC) 30 which is incorporated in the control panel 4, in the embodiment.

First Embodiment

FIG. 6, FIG. 7

Figure 6:
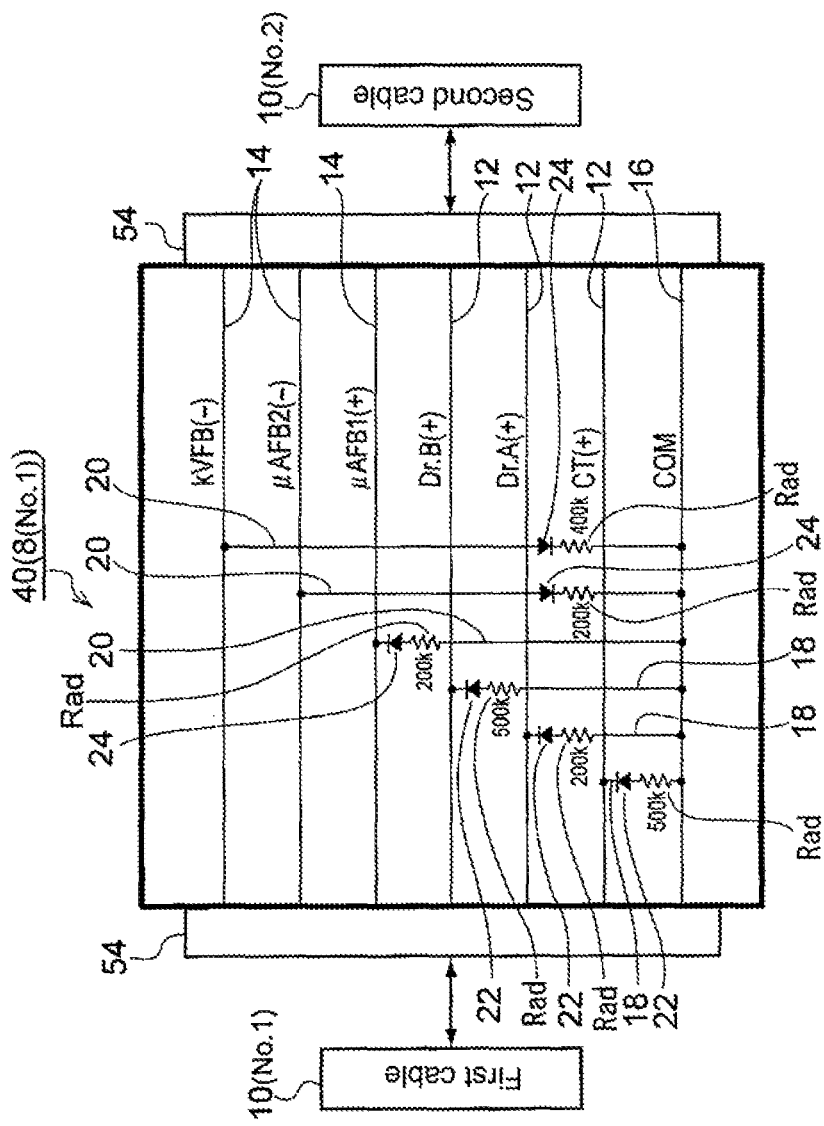
FIG. 6 is a diagram for explaining an internal structure of a first connecting section (a first relay box) of an electrostatic coating cable maintenance device of a first embodiment.
Figure 7:
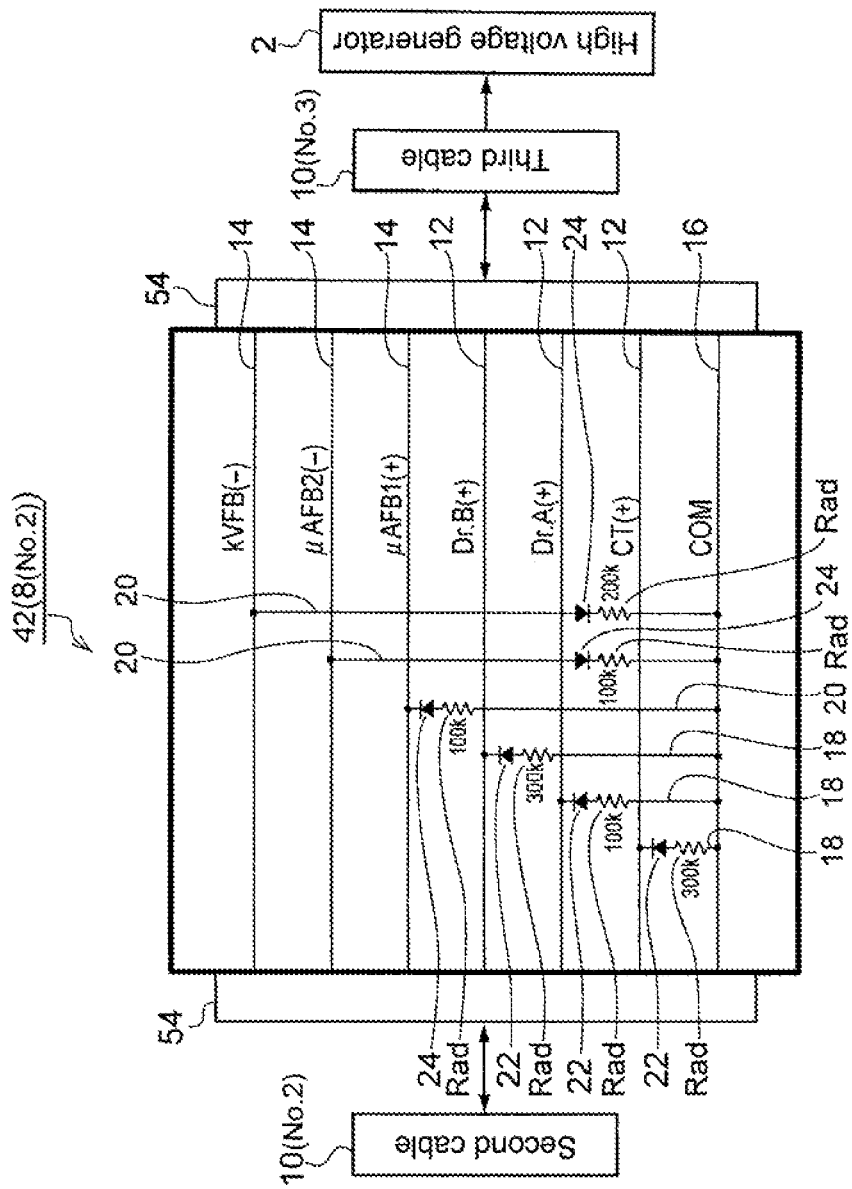
FIG. 7 is a diagram for explaining an internal structure of a second connecting section (a second relay box) of the electrostatic coating cable maintenance device of the first embodiment.

FIG. 6 and FIG. 7 show a first embodiment. FIG. 6 is a diagram showing an internal structure of the first relay box 40 which configures the aforementioned first connecting section 8 (No. 1). FIG. 7 is a diagram showing an internal structure of the second relay box 42 that configures the aforementioned second connecting section 8 (No. 2). Reference numeral 54 shown in each of FIG. 6 and FIG. 7 designates a connector.

Referring to FIG. 6 and FIG. 7, in each of the first and the second relay boxes 40 and 42, each of three power supply lines 12 is connected to the common ground line 16 by a first inspection line 18, and each of three signal lines 14 is connected to the common ground line 16 by a second inspection line 20. The first and the second diodes 22 and 24 are interposed respectively in the first and the second inspection lines 18 and 20. The first and the second diodes 22 and 24 respectively inhibit a current from flowing through the first and the second inspection lines 18 and 20 during an operation of the electrostatic coater 1.

Referring to FIG. 5 described above and FIG. 6 and FIG. 7 showing the first embodiment, reference letters "CT", "Dr.A", and "Dr.B" mean powers (plus voltages) to be supplied to the high voltage generator 2. Reference letter "μAFB1" means a signal obtained by converting the current flowing to the high voltage generator 2 during an operation of the electrostatic coater 1 into a voltage. The signal of "μAFB1" is fed back to the control panel 4 with a positive voltage during an operation of the electrostatic coater 1. Reference letter "kVFB" means an output of the high voltage generator 2, namely, a signal of a negative voltage obtained by reducing the high voltage with negative polarity. For example, when the output of the high voltage generator 2 is minus 90,000 volts, "kVFB" is minus 9 volts. Reference letter "μAFB2" means a signal obtained by converting a leakage current to a metallic case that surrounds the high voltage generator 2 into a negative voltage.

In the first and the second inspection lines 18 and 20, additional resistors $R_{ad}$ are respectively connected in series to the diodes 22 and 24. In FIG. 6 and FIG. 7, specific resistance values are described next to the additional resistors $R_{ad}$. The specific resistance values are determined based on an experiment.

More specifically, the resistance values of the aforementioned additional resistors $R_{ad}$ are set as follows. Namely, the resistance values of the additional resistors $R_{ad}$ are set so that a feedback voltage $V_a$ in the case in which a problem occurs to the first divided cable 10 (No. 1) is at a potential higher than a feedback voltage at a time of all the divided cables 10 (No. 1 to No. 3) being normal, the feedback voltage $V_a$ in a case in which a problem occurs to the second and the third divided cables 10 (No. 2 and No. 3) is at a potential lower than the feedback voltage at the time of all the divided cables 10 (No. 1 to No. 3) being normal, and further, a clear difference appears between the feedback voltages $V_a$ at the time of a problem occurring to the second divided cable 10 (No. 2), and at a time of a problem occurring to the third divided cable 10 (No. 3).

Figure 2:
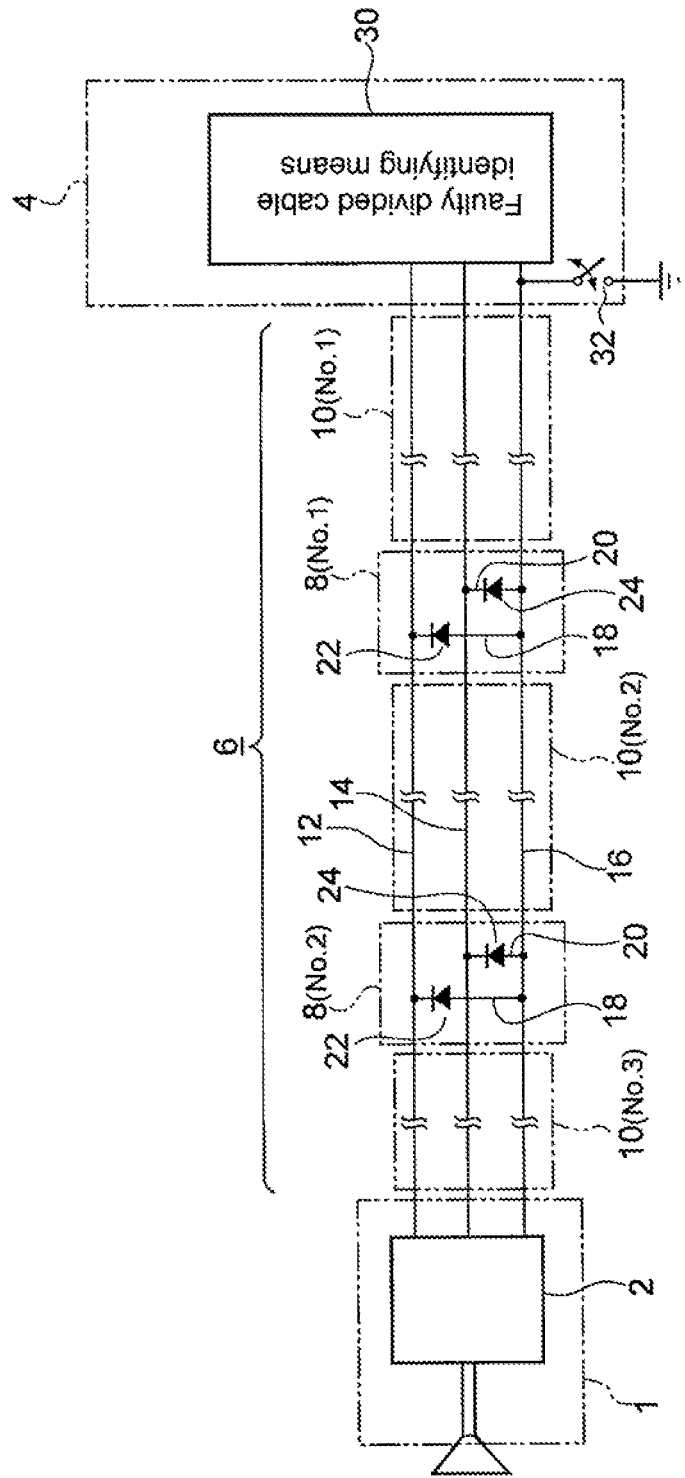
FIG. 2 is a diagram for explaining a basic concept of the present invention.
Figure 3:
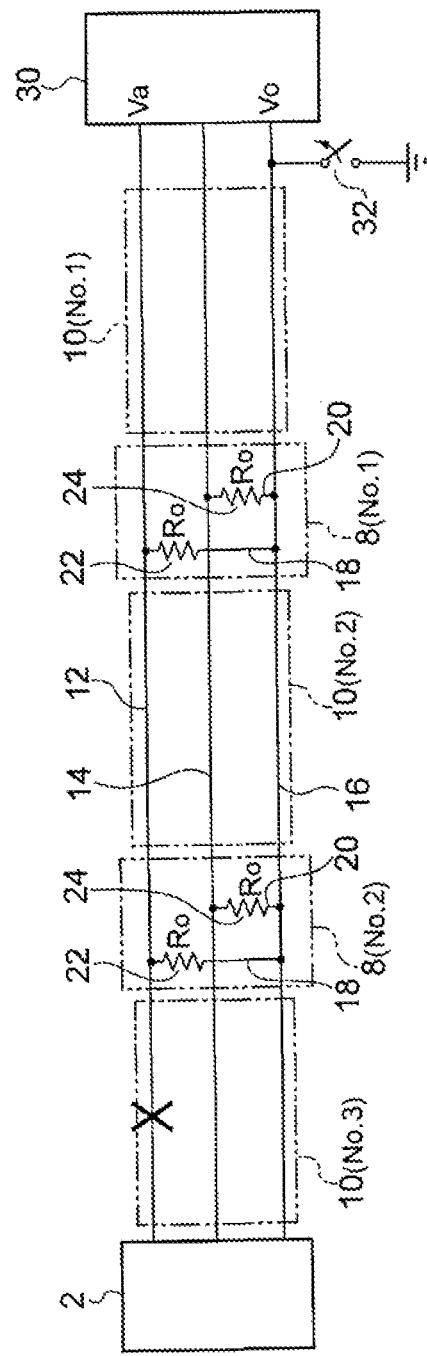
FIG. 3 is an operation explanatory diagram for explaining an operation of the present invention by simplification, with a case in which a problem occurs to a divided cable which is the closest to a high voltage generator taken as an example.
Figure 4:
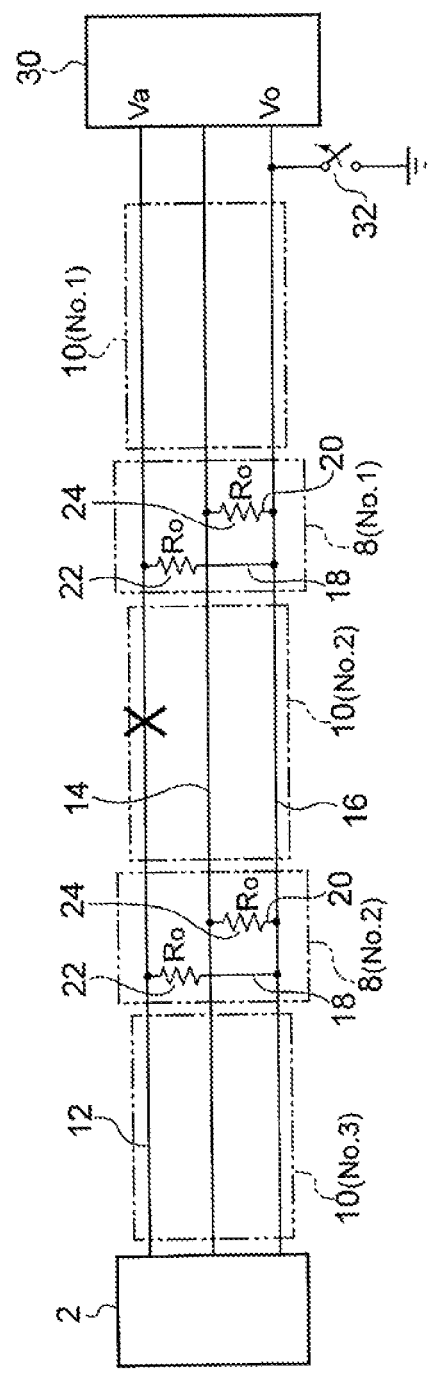
FIG. 4 is an operation explanatory diagram for explaining an operation of the present invention by simplification with a case in which a problem occurs to a second divided cable taken as an example.

The electrostatic coating cable maintenance device of the embodiment is executed to find out abnormality of the divided cable 8 or identify an abnormal divided cable 8, when abnormality occurrence is displayed on the control panel 4 during an operation of the electrostatic coater 1, and while the electrostatic coater 1 is stopping before start of the electrostatic coater 1 or the like. Prior to the execution, the switch 32 which is described with reference to FIG. 2 to FIG. 4 is turned off to cut off grounding of the common ground line 16, and a positive inspection voltage of several tens of volts, for example, is applied to the common ground line 16.

According to the electrostatic coating cable maintenance device of the embodiment, when a problem occurs to any one of the first to the third divided cables 10 (No. 1 to No. 3), the feedback voltage $V_a$ thereof is at a potential different from the potential of the feedback voltage at the time of all the divided cables 10 (No. 1 to No. 3) being normal as described above. The feedback voltage $V_a$ differs depending on to which one of the first to the third divided cables 10 (No. 1 to No. 3) the problem occurs. With use of the difference, identification of any one of the first to the third divided cables 10 (No. 1 to No. 3) to which a problem occurs is performed by the faulty divided cable identifying means (high voltage controller IC) 30, and display thereof is displayed on a monitor of the control panel 4. As a feedback signal at a time of application of a positive inspection voltage of several tens of volts, for example, to the common ground line 16, it may be detected to which one(s) of the first to the third divided cables 10 (No. 1 to No. 3) a problem occurs, based on a difference in a current value, instead of the feedback voltage $V_a$.

An operator immediately finds which divided cable is abnormal by looking at the display on the monitor of the control panel 4, and the electrostatic coating cable 6 can be restored early by replacing the divided cable 10 with a problem immediately.

As described above, when the electrostatic coater 1 is operated, the first and the second diodes 22 and 24 can inhibit a current from flowing through the first and the second inspection lines 18 and 20, and thereby, the electrostatic coater 1 can be normally operated.

Second Embodiment

FIG. 8

Figure 8:
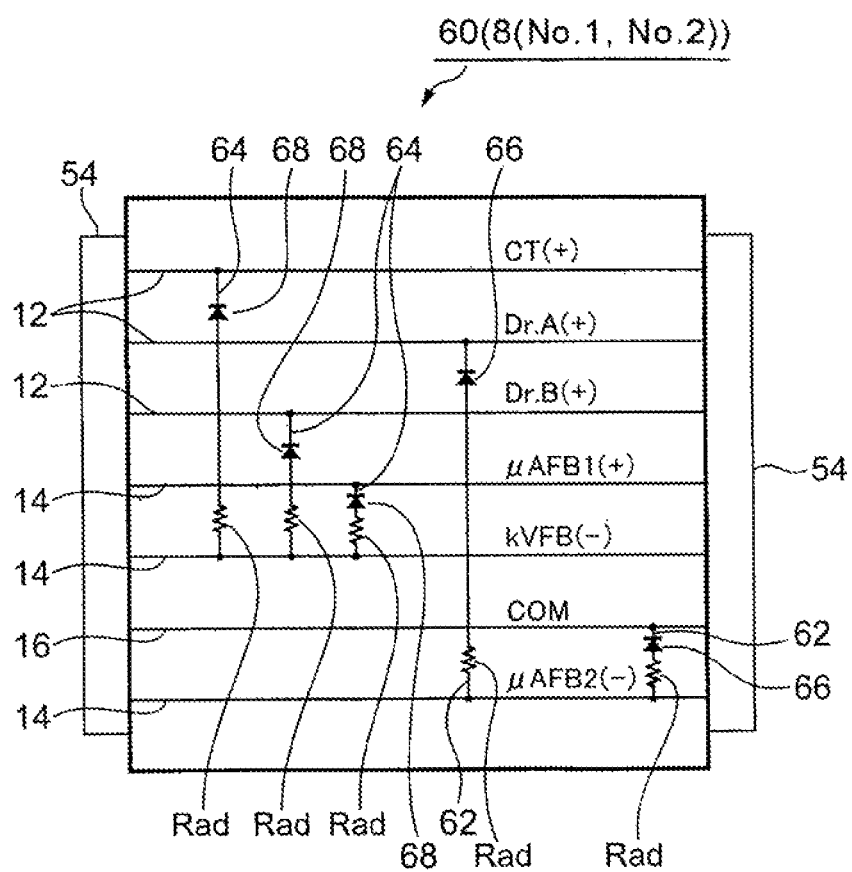
FIG. 8 is a diagram for explaining internal structures of a first and a second connecting sections (relay boxes) of an electrostatic coating cable maintenance device of a second embodiment.

FIG. 8 shows an internal structure of a relay box 60 included in a second embodiment. The relay box 60 that configures each of the first connecting section 8 (No. 1) and the second connecting section 8 (No. 2) described above has a substantially same configuration. The relay box 60 has the three power supply lines 12 which supply power (positive voltage) to the high voltage generator 2 at the time of an operation of the electrostatic coater 1, the common ground line 16, and the three signal lines 14. At the time of an operation of the electrostatic coater 1, a positive voltage is fed back to the control panel 4 through the μAFB1 line of the three signal lines 14, a negative voltage is fed back to the control panel 4 through the kVFB line, and a negative voltage is fed back to the control panel 4 through the μAFB2 line.

In the relay box 60, the three power supply lines 12 and the signal line 14 of μAFB1, and the common ground line 16 with positive voltages (during an operation of the electrostatic coater 1) are connected to either of the two signal lines 14 of μAFB2 and kVFB with negative voltages (during an operation of the electrostatic coater 1) by third and fourth inspection lines 62 and 64. In an example of FIG. 8, a Dr.A line which is the power supply line 12 and the common ground line 16 are connected to the μAFB2 line which is the signal line 14 with a negative voltage (during an operation of the electrostatic coater 1) by the third inspection lines 62. A CT line and a Dr.B line that are the power supply lines 12 and the μAFB1 signal line 14 with a positive voltage (during an operation of the electrostatic coater 1) are connected to the kVFB line which is the signal line 14 with a negative voltage (during an operation of the electrostatic coater 1) by the fourth inspection lines 64. As a modification, the CT power supply line 12 may be connected to the μAFB2 signal line 14, and the common ground line 16 may be connected to the kVFB signal line 14, for example. As a matter of course, the Dr.A power supply line 12 may be connected to the kVFB signal line 14, and the μAFB1 signal line 14 may be connected to the μAFB2 signal line 14.

In the third and the fourth inspection lines 62 and 64, diodes 66 and 68 that inhibit a current from flowing through the third and the fourth inspection lines 62 and 64 during an operation of the electrostatic coater 1 are interposed. The additional resistors $R_{ad}$ are preferably connected in series to the diode 66 and 68. The resistance values of the additional resistors $R_{ad}$ which are connected to the third and the fourth inspection wires 62 and 64 are optional. As described in the above described first embodiment, the resistance values of the additional resistors $R_{ad}$ which are connected to the third and the fourth inspection lines 62 and 63 can be set so that a clear difference appears in the feedback voltage $V_a$ in the case in which a problem occurs to the first divided cable 10 (No. 1), the second divided cable 10 (No. 2) or the third divided cable 10 (No. 3).

In the second embodiment, the electrostatic coating cable maintenance device of the embodiment is also executed to find abnormality of the divided cable 8 or to identify the abnormal divided cable 8, at a time of abnormal occurrence being displayed on the control panel 4 during an operation of the electrostatic coater 1, and during stoppage of the electrostatic coater 1 before start of the electrostatic coater 1 or the like, similarly to the aforementioned first embodiment. Prior to the execution, the switch 32 which is described with reference to FIG. 2 to FIG. 4 is turned off to cut off grounding of the common ground line 16, and a positive inspection voltage of several tens of volts, for example, is applied to the two signal lines 14 that are the μAFB2 line and kVFB line with negative voltages during an operation of the electrostatic coater 1.

According to the second embodiment, in the case in which a problem occurs to any divided cable of the first to the third divided cables 10 (No. 1 to No. 3) as described above, including the time when the common ground line 16 is almost broken, the feedback voltage $V_a$ thereof is at a potential different from the feedback voltage at the time of all the divided cables 10 (No. 1 to No. 3) being normal. The feedback voltage $V_a$ differs depending on to which one of the first to the third divided cables 10 (No. 1 to No. 3) the problem occurs. With use of the difference, identification of the divided cable to which the problem occurs out of the first to the third divided cables 10 (No. 1 to No. 3) is performed by the faulty divided cable identifying means (high voltage controller IC) 30, and display thereof is displayed on a monitor of the control panel 4. An operator immediately finds which divided cable is abnormal by looking at the display on the monitor of the control panel 4, and can restore the electrostatic coating cable 6 early by replacing the divided cable 10 with the problem immediately.

In the second embodiment, as the feedback signal at the time of the positive inspection voltage of several tens of volts, for example, being applied to the two signal lines 14 of the μAFB2 line and the kVFB line, it may be detected to which one of the first to the third divided cables 10 (No. 1 to No. 3) a problem occurs, based on a difference in the current values, instead of the feedback voltage $V_a$.

In the second embodiment, as described above, when the electrostatic coater 1 is operated, the diodes 66 and 68 also can inhibit a current from flowing through the third and the fourth inspection lines 62 and 64, and thereby, the electrostatic coater 1 can be normally operated.

Third Embodiment

FIG. 9

Figure 9:
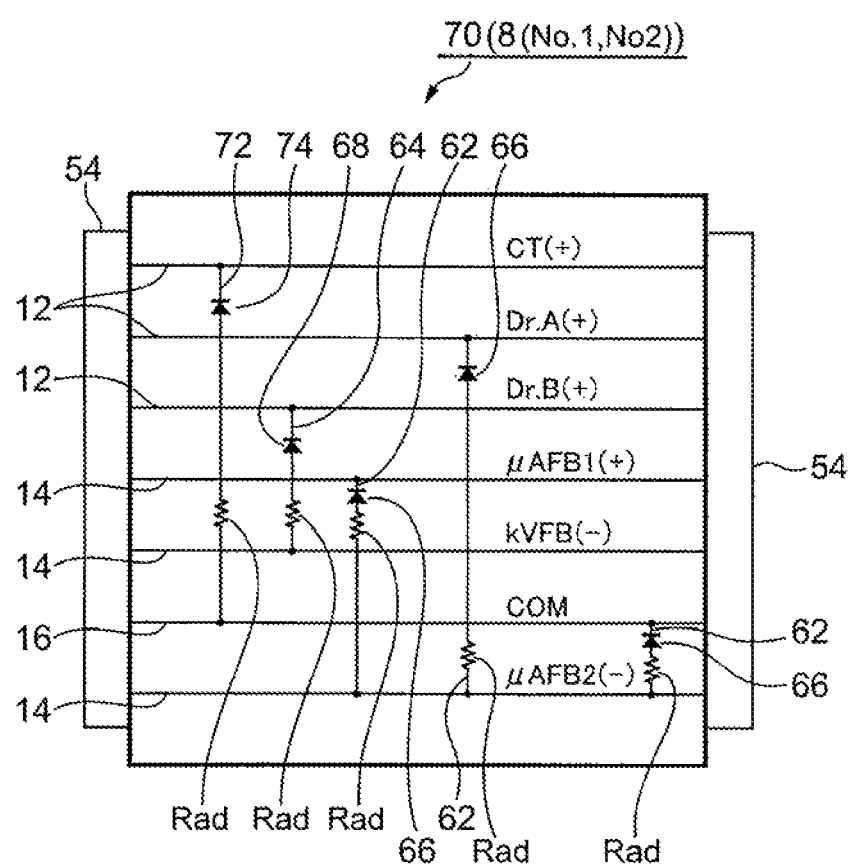
FIG. 9 is a diagram for explaining internal structures of a first and a second connecting sections (relay boxes) of an electrostatic coating cable maintenance device of a third embodiment.

FIG. 9 shows an internal structure of a relay box 70 included in a third embodiment. The relay box 70 that configures each of the first connecting section 8 (No. 1) and the second connecting section 8 (No. 2) described above has substantially the same configuration, and the relay box 70 included in the third embodiment is also a modification of the aforementioned second embodiment (FIG. 8).

Referring to FIG. 9, the Dr.B line 12 which is the power supply line 12 is connected to the kVFB line which is the signal line 14 with a negative voltage (during an operation of the electrostatic coater 1) by the third inspection line 62, and a diode 66 and preferably the resistor Rad are connected to the third inspection line 62. Further, the CT line which is the power supply line 12 is connected to the common ground line 16 via a fifth inspection line 72, and a diode 74 and preferably the resistor Rad are connected in series to the fifth inspection line 72. The other configuration is the same as that of the second embodiment (FIG. 8).

As a person skilled in the art could understand from the above description of the embodiments, the present invention teaches the following. Namely, the two lines having a potential difference (during an operation of the electrostatic coater 1) are connected by the inspection line including a diode, and the diode is interposed in the inspection line, whereby a current is inhibited from flowing through the inspection line during an operation of the electrostatic coater 1. Accordingly, if there is a potential difference between the potentials of the two lines with positive potentials during an operation of the electrostatic coater 1, the two lines may be connected by the inspection line including a diode. Likewise, if there is a potential difference between the potentials of the two lines with negative polarities during an operation of the electrostatic coater 1, the two lines may be connected by the inspection line including a diode. Subsequently, a voltage is added to the line with a relatively lower potential (during an operation of the electrostatic coater 1) out of the two lines connected by the inspection line, during stoppage of the operation of the electrostatic coater 1 (a voltage is added to the diode in the forward direction), whereby a failure in each of the lines can be detected.

The present invention is applicable to a rotary atomization type and a spray type electrostatic coaters. Further, the present invention is applicable to electrostatic coaters with a liquid coating material and a powder coating material. Further, the present invention is applicable to an electrostatic coater with a conductive liquid coating material (more specifically, a water base paint), besides a coating material using a thinner as a solvent.

What is claimed is:

1. An electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line and a ground line, and the power supply line or the signal line that configures the cable being brought into a state immediately before breakage, wherein in a plurality of lines that configure the power supply line, the signal line and the ground wire, two lines having a potential difference during an operation of the electrostatic coater are set as a pair, and the two lines that configure each pair are connected by an inspection line, a diode is interposed in the inspection line, and the diode inhibits a current from flowing between the two lines during the operation of the electrostatic coater, the electrostatic coating cable maintenance device comprises faulty divided cable identifying means that, during stoppage of the operation of the electrostatic coater, applies a voltage to the inspection line connecting the two lines of each pair to pass a current through the inspection line, detects feedback signals that return from the respective two lines, and identifies the divided cable which is brought into a state immediately before breakage based on abnormality of the feedback signals, and the inspection line and the diode are disposed in a cable connecting section that connects the divided cables adjacent to each other.

2. The electrostatic coating cable maintenance device according to claim 1,
wherein a resistor is interposed in the inspection line, and the resistor and the diode are connected in series.

3. An electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line and a ground line, and the power supply line or the signal line that configures the cable being brought into a state immediately before breakage, the electrostatic coating cable maintenance device comprising:
a first inspection line that connects the ground line and the power supply line;
a second inspection line that connects the ground line and the signal line;
a first diode that is interposed in the first inspection line, and cuts off a flow of a current between the power supply line and the ground line during an operation of the electrostatic coater;
a second diode that is interposed in the second inspection line, and cuts off a flow of a current between the signal line and the ground line during the operation of the electrostatic coater;
a ground switch that is provided in the ground line, and can switch to a first mode that grounds the ground line, and a second mode that applies a voltage to the ground line; and
faulty divided cable identifying means that, during stoppage of the operation of the electrostatic coater, detects feedback signals that return from the power supply line and the signal line when a voltage is applied to the ground line in a state in which the switch is switched to the second mode from the first mode, and identifies a divided cable which is brought into a state immediately before breakage based on abnormality of the feedback signals,
wherein the first and the second inspection lines and the first and the second diodes are disposed in a cable connecting section that connects the divided cables adjacent to each other.

4. An electrostatic coating cable maintenance device for identifying a divided cable that is brought into a state immediately before breakage out of a plurality of divided cables that configure an electrostatic coating cable that electrically connects an electrostatic coater containing a high voltage generator with a control panel that controls the electrostatic coater, the electrostatic coating cable including a power supply line that supplies power to the high voltage generator, a signal line in which a signal at a potential with polarity opposite to polarity of the power supply line flows during an operation of the electrostatic coater, and a ground line, and the power supply line or the signal line that configures the cable being brought into a state immediately before breakage, the electrostatic coating cable maintenance device comprising:
a third inspection line that connects the signal line and the power supply line during the operation of the electrostatic coater;
a fourth inspection line that connects the signal line and the ground line during the operation of the electrostatic coater;
a third diode that is interposed in the third inspection line, and cuts off a flow of a current between the power supply line and the signal line during the operation of the electrostatic coater;
a fourth diode that is interposed in the fourth inspection line, and cuts off a flow of a current between the signal line and the ground line during the operation of the electrostatic coater;
a ground switch that is provided in the ground line, and can switch to a first mode that grounds the ground line, and a second mode that applies a voltage to the ground line; and
faulty divided cable identifying means that, during stoppage of the operation of the electrostatic coater, detects feedback signals that return from the power supply line and the ground line when a voltage is applied to the signal line in a state in which the switch is switched to the second mode from the first mode, and identifies a divided cable which is brought into a state immediately before breakage based on abnormality of the feedback signal,
wherein the third and the fourth inspection lines and the third and the fourth diodes are disposed in a cable connecting section that connects the divided cables adjacent to each other.

5. The electrostatic coating cable maintenance device according to claim 4,
wherein the electrostatic coating cable further comprises a second signal line in which a signal at a potential with same polarity as polarity of the power supply line flows during the operation of the electrostatic coater, besides the signal line in which a signal at a potential with polarity opposite to polarity of the power supply line flows during the operation of the electrostatic coater,
the electrostatic coating cable maintenance device further comprising:
a fifth inspection line that connects the second signal line and the signal line in which a signal at a potential with polarity opposite to the polarity of the power supply line flows; and
a fifth diode that is interposed in the fifth inspection line, and cuts off a flow of a current between the second signal line and the signal line in which a signal at the potential with polarity opposite to the polarity of the power supply line flows during the operation of the electrostatic coater.

6. The electrostatic coating cable maintenance device according to claim 5,
wherein an additional resistor is connected in series with the fifth diode in the fifth inspection line.

* * * * *